United States Patent
Madeira

(10) Patent No.: US 12,053,382 B2
(45) Date of Patent: Aug. 6, 2024

(54) SYSTEM AND METHODS FOR PERCUTANEOUS MECHANICAL AND/OR NEURAL INTERFACE

(71) Applicant: Robert Madeira, Allentown, PA (US)

(72) Inventor: Robert Madeira, Allentown, PA (US)

( * ) Notice: Subject to any disclaimer, the term of this patent is extended or adjusted under 35 U.S.C. 154(b) by 0 days.

(21) Appl. No.: 18/141,370

(22) Filed: Apr. 29, 2023

(65) Prior Publication Data
US 2023/0263635 A1    Aug. 24, 2023

Related U.S. Application Data

(60) Division of application No. 17/734,044, filed on Apr. 30, 2022, now Pat. No. 11,678,991, which is a
(Continued)

(51) Int. Cl.
*A61F 2/28* (2006.01)
*A61F 2/38* (2006.01)
(Continued)

(52) U.S. Cl.
CPC .......... *A61F 2/2814* (2013.01); *A61F 2/3859* (2013.01); *A61F 2/389* (2013.01);
(Continued)

(58) Field of Classification Search
CPC ...... A61M 2025/0056; A61M 39/0247; A61M 25/007; A61M 2039/027; A61M 2025/0031; A61M 2025/0057; A61M 2025/006; A61M 2039/0261; A61M 2039/0273; A61M 2039/0276; A61M 2039/0288; A61M 25/003; A61M 25/0045; A61M 25/02; A61M 39/20; A61F 2002/7887; A61F 2/2814; A61F 2/3859; A61F 2/389; A61F 2/60; A61F 2/78; A61F 2002/30884; A61F 2/28; A61F 2/72; A61F 2002/2825; A61F 2002/2871; A61F 2002/2896; A61F 2002/30331; A61F 2002/30433; A61F 2002/30469; A61F 2002/30481; A61F 2002/30495;
(Continued)

(56) References Cited

U.S. PATENT DOCUMENTS

| | | | |
|---|---|---|---|
| 2011/0054507 A1* | 3/2011 | Batten | A61B 17/32002 606/170 |
| 2011/0110888 A1* | 5/2011 | Xian | A61L 27/22 514/8.5 |

\* cited by examiner

*Primary Examiner* — Brandy S Lee

(57) ABSTRACT

A system for attachment of a device to a bone is provided. The system includes an internal axial rod with a proximal and distal end that is configured to be inserted and secured into a bone cavity's distal end. The system can also include an internal-external transfer rod with a proximal and distal end mounted into the distal end of the axial rod and a central channel extending through the transfer rod from the proximal end to the distal end and a plurality of attachment rings for attaching at least one tissue or muscle group to the transfer rod. The system also includes a bio-compatible and bio-occlusive artificial membranes (BIOCAMS) lamina, wherein the lamina includes either a polyetheretherketone (PEEK) mesh, a biocompatible polymer, a carbon fiber polymer, an artificial tissue polymer, molded donor tissue, allogenic tissue, a collagen/hyaluronic acid-based tissue, or connective tissue biosynthetic substrate material suitable as webbing.

11 Claims, 11 Drawing Sheets

Related U.S. Application Data continuation-in-part of application No. 16/852,576, filed on Apr. 20, 2020, now Pat. No. 11,406,816, which is a division of application No. 15/707,185, filed on Sep. 18, 2017, now Pat. No. 10,675,456.

(60) Provisional application No. 62/495,625, filed on Sep. 20, 2016.

(51) Int. Cl.
| | |
|---|---|
| *A61F 2/60* | (2006.01) |
| *A61F 2/78* | (2006.01) |
| *A61M 25/00* | (2006.01) |
| *A61M 25/02* | (2006.01) |
| *A61M 39/20* | (2006.01) |
| *A61F 2/30* | (2006.01) |
| *A61M 39/02* | (2006.01) |
| *A61N 1/05* | (2006.01) |

(52) U.S. Cl.
CPC .................. *A61F 2/60* (2013.01); *A61F 2/78* (2013.01); *A61M 25/003* (2013.01); *A61M 25/0045* (2013.01); *A61M 25/007* (2013.01); *A61M 25/02* (2013.01); *A61M 39/20* (2013.01); *A61F 2002/2825* (2013.01); *A61F 2002/30602* (2013.01); *A61F 2002/30884* (2013.01); *A61F 2002/607* (2013.01); *A61F 2002/608* (2013.01); *A61F 2002/7887* (2013.01); *A61M 2025/0031* (2013.01); *A61M 2025/0056* (2013.01); *A61M 2025/0057* (2013.01); *A61M 2025/006* (2013.01); *A61M 39/0247* (2013.01); *A61M 2039/0261* (2013.01); *A61M 2039/027* (2013.01); *A61M 2039/0273* (2013.01); *A61M 2039/0276* (2013.01); *A61M 2039/0288* (2013.01); *A61N 1/0558* (2013.01)

(58) Field of Classification Search
CPC ...... A61F 2002/305; A61F 2002/30505; A61F 2002/30507; A61F 2002/30602; A61F 2002/607; A61F 2002/608; A61N 1/0558; A61N 1/36057
See application file for complete search history.

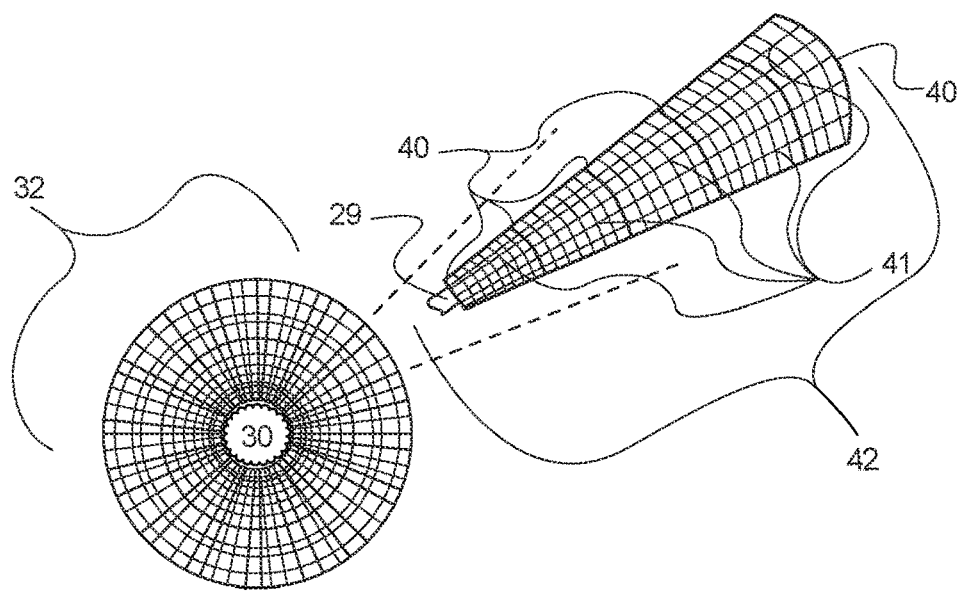
FIG. 6 A
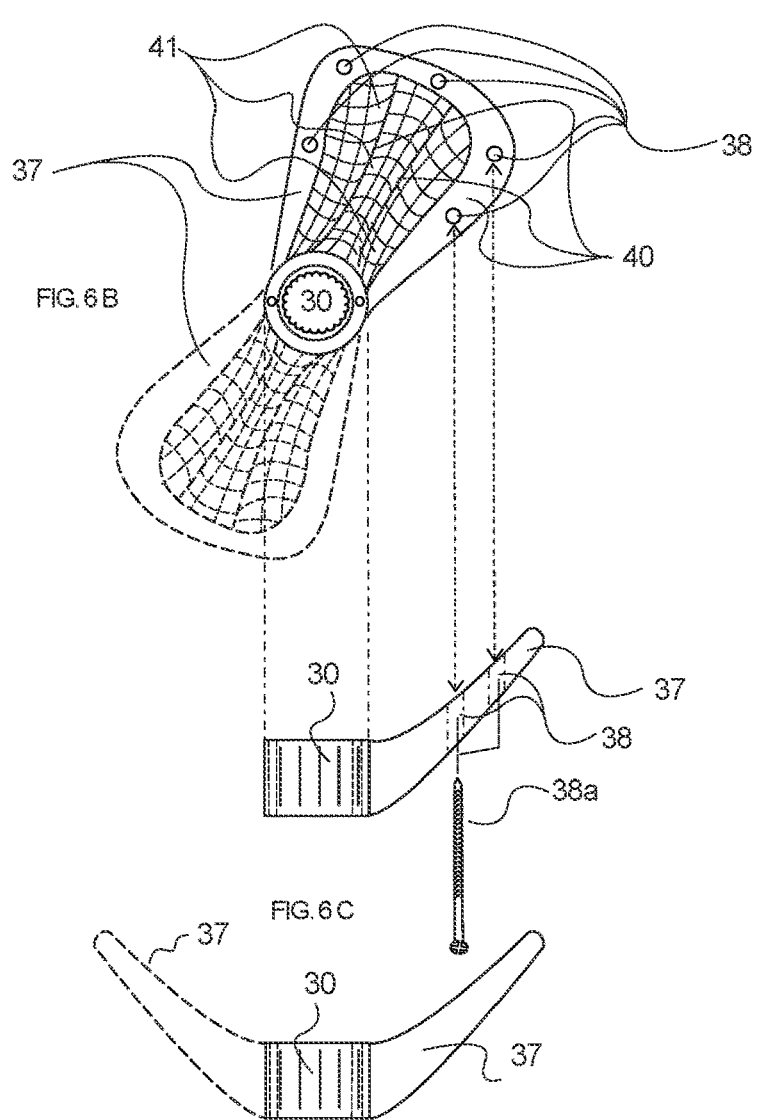
FIG. 6 B
FIG. 6 C

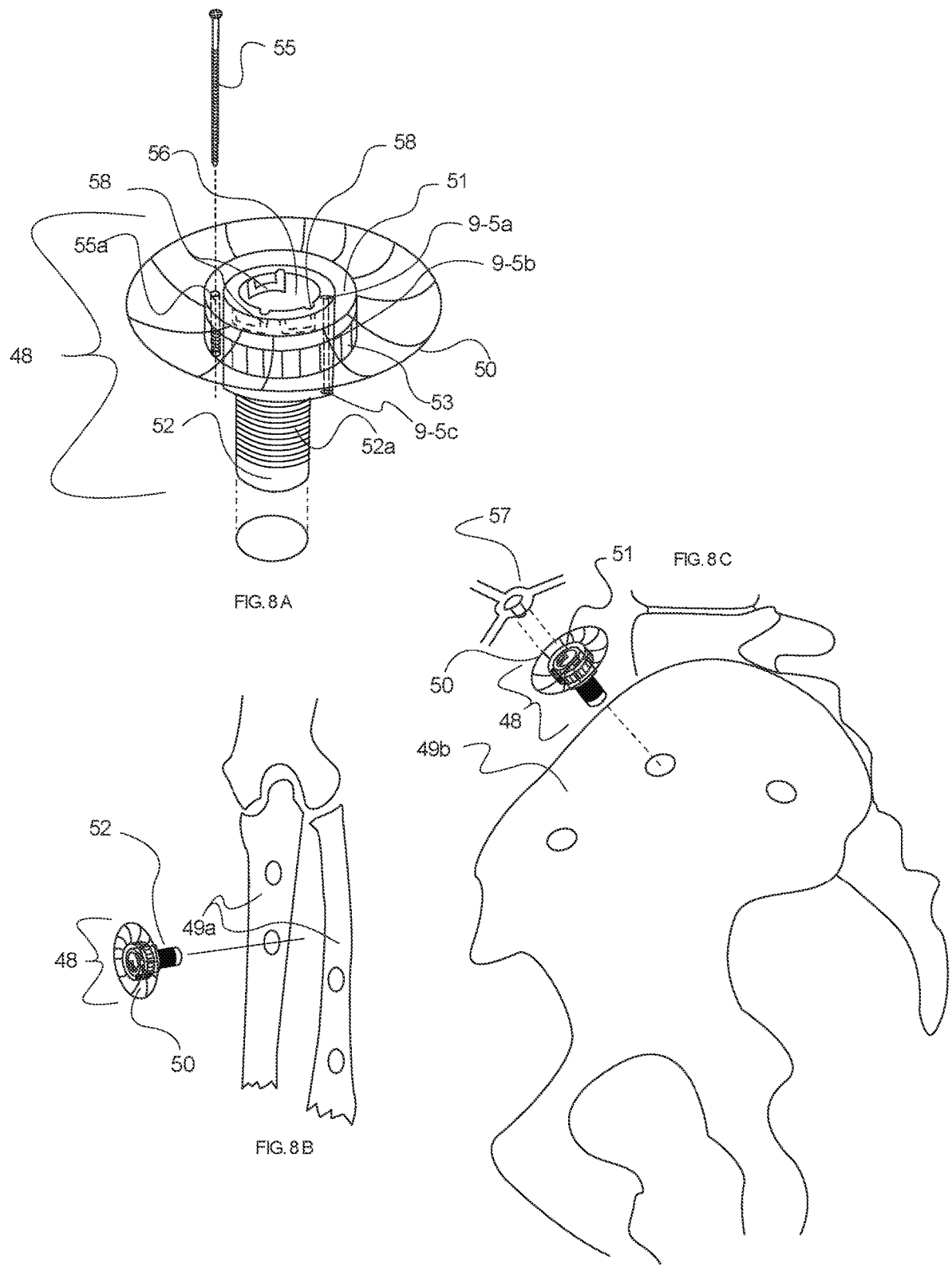

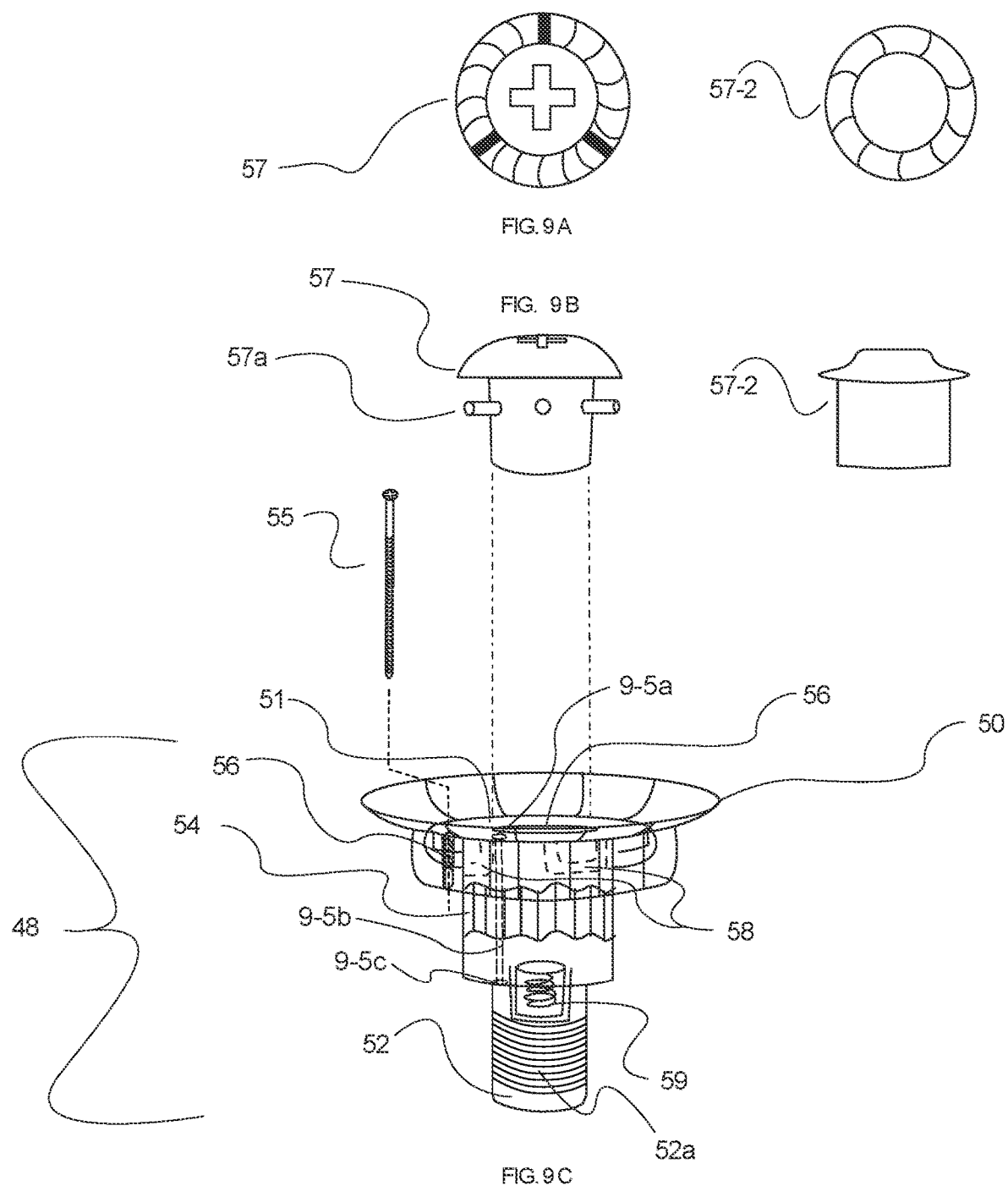

SYSTEM AND METHODS FOR PERCUTANEOUS MECHANICAL AND/OR NEURAL INTERFACE

RELATED APPLICATIONS

This application claims priority to U.S. Non-Provisional application Ser. No. 17/734,044 filed Apr. 30, 2022. The entire contents of the above application are hereby incorporated by reference as though fully set forth herein. Further, this application claims priority to U.S. Non-Provisional application Ser. No. 16/852,576 filed Apr. 20, 2020. The entire contents of the above application are hereby incorporated by reference as though fully set forth herein. Also, this application claims priority to U.S. Non-Provisional application Ser. No. 15/707,185 filed Sep. 18, 2017. The entire contents of the above application are hereby incorporated by reference as though fully set forth herein. And, this application claims priority to U.S. Provisional Application No. 62/495,625 filed Sep. 20, 2016. The entire contents of the above application are hereby incorporated by reference as though fully set forth herein.

FIELD

The present invention relates to the field of human-machine interfaces. More specifically, the present invention relates to mechanical-including air and fluid-interface, and/or neuronal interface and/or sensory/biometric interface connection systems for attachment of objects/systems to the body.

BACKGROUND

There are numerous medical devices that attach to the body or are transcutaneously placed for short- or long-term applications, such as a peripheral intravenous site, a suprapubic catheter, a triple lumen venous catheter, feeding tubes, a peritoneal dialysis catheter, or a pleural based drainage catheter, as well as external orthopedic fixation hardware. One set of devices that attach externally to human limbs or bodies are prosthetics, usually for people with amputation or limb malformations.

Amputation is the absence or removal of a partial or entire limb by congenital status, disease, medical illness, trauma or surgery. A prosthetic is an artificial device that replaces an amputated or otherwise missing body part, which may be amputated or lost through trauma, disease, or congenital conditions.

BRIEF SUMMARY OF THE INVENTION

There are several ways that a prosthesis can be attached to a limb vestige or host body. It may be held on with suction, a locking pin, or with a harness. Each method has advantages and drawbacks. A harness can be bulky and not move as well as the other systems. A locking pin may cause irritation where it contacts the stump. Suction is generally considered the best choice, but the user must put the prosthesis on accurately in order to get secure suction. None of these methods are durable for wearing a prosthesis for long periods of time.

These current means and methods of prosthetic attachment are not conducive to use for a variety of other potential exterior attachments, other than standard prosthetic devices, which typically are meant to somewhat mimic natural limb function. Alternative external prosthetic devices could also theoretically include a wide variety of powered and/or computerized tools, for example.

Further, although external capture of specific muscle fiber twitches has enabled some current prosthetics to function with some increased functional capacity, no current prosthetic devices or systems are able to directly interface with the neuronal signaling of specific nerve bundles and fibers which were in actual or theoretical direct distribution to the lost functional capacity, to capture and utilize nervous system signaling in any meaningful fashion. Further, the current means of percutaneous attachment are generally not fully bio-occlusive or biocompatible in terms of their ability to semi-permanently conjoin with the host body's tissues and therefore have significant risk of localized inflammation or risk of infection from external sources, especially if left in place for an extended time or in dirty environments. Thus, it would be useful to have a new system and method to improve percutaneous attachment of medical devices, in terms of mechanical attachment—which includes air and fluids interface, neurologic interface and sensory/biometric data interface.

These would include variations on the diverse tubes and catheters discussed above. This also includes a system and method to percutaneously provide a range of degrees of limb function after amputation to that also allows a significantly higher degree of human-machine interface. It is an object of the present invention to provide a new system and method for improving percutaneous, bio-compatible and bio-occlusive attachment of medical devices including a wide array of tubes and catheters, as well as the percutaneous attachment of non-medical objects to the body, and to combine multiple percutaneous connectivity functions to allow semi-permanent connection of a prosthetic limb or non-limb attachment to provide a significant range of functions from simple to highly complex human-machine interfaces.

These percutaneous interfaces potentially include, mechanical interfaces, including air and fluid interfaces, neuronal interfaces, and sensory/biometric interfaces. An embodiment of the present invention is a system to provide placement of percutaneous catheters or tubes which have (a) bio-compatible and bio-occlusive artificial membranes (BIOCAMS) tissue attachment lamina to allow for attachment to any epithelial, mesothelial or endothelial derived tissue layer such as dermal, fascial, endothelial, mucosal, and pleural tissue layers. BIOCAM lamina are generally flat membranes or mesh works, of any shape or outline.

"PEEK" stands for polyetheretherketone, which is a semi-crystalline, high temperature plastic. It is chosen to represent any selection of a large family of bio-neutral polymers available for surgical implantation purposes. The BIOCAM lamina can be constructed either from PEEK, another bio-compatible metallic mesh, a biocompatible polymer, a carbon fiber polymer, an artificial tissue polymer, molded donor tissues, allogeneic tissue, a collagen/hyaluronic acid based tissue, and any other equivalent connective tissue biosynthetic substrate material suitable for surgical implantation into the body.

The BIOCAM lamina can further include any formation of transitional webbed areas interlaced across a biocompatible material scaffolding and may allow for a range of degrees of bio integration or bio-dissolution. The webbed area can include a generally central area that is more densely woven and has a decreasing density of webbing as it approaches the outer edge of the lamina. The host body's tissue layers can be sutured or glued onto and into the webbed areas of the lamina. The lamina materials may further include surface coated molecules of epithelial growth factors or other growth factors. Embodiments of the present invention include potentially multi-flanged biocompatible linkages (BIOCLS) for attachment to tendon & muscle groups for prolonged or permanent periods of placement.

BIOCLS generally act as leveraged linkage between a generally central mechanical hub and tendons or muscles. BIOCLS are generally made of similar materials as BIO-CAMS. BIOCAMS and BIOCLS allow for "cytointegration" and "organointegration" of the BIOCAMS and BIO-CLS with bodily tissues. An embodiment of the present invention is a system for attachment of a device to a bone, via an osseointegrated implant. It includes generally an axially oriented solely internal (SI) long bone implant-rod inserted into the long bone medullary cavity; the distal end of the SI long bone implant-rod exits the long bone but remains surrounded by the soft tissues of the limb. The distal end of the SI long bone implant-rod may include a rectangular, hexagonal, or other securing shape region, which include star shaped driver terminals, square blocks, rectangular blocks, hex screws, torx fasteners, and/or other screw drives for mechanical turning of the implant-rod during surgical implantation.

The SI long bone axial implant-rod is then mechanically joined to an internal-external (IE) transfer rod implant, which itself penetrates all overlaying tissue layers, and may include BIOCAM lamina and/or rings or BIOCL for attaching to any soft tissue of the limb and has a distal portion that protrudes from the limb and allows for an exterior bodily attachment of a prosthetic. The mechanical connection between the osseointegrated SI long bone axial implant-rod and the IE transfer implant-rod may be via a hollow channel in the SI long bone axial implant-rod which allows a mated insertion of the proximal portion of the IE transfer implant-rod within the central channel of the SI long bone axial implant-rod to which it is mounted.

The distal end of the IE transfer implant-rod is external to the body and may include a rectangular, hexagonal, or other securing shape region, which include star shaped driver terminals, square blocks, rectangular blocks, hex screws, torx fasteners, and/or other screw drives for mechanical turning of the implant-rod during surgical implantation. The distal-terminal end of the IE transfer implant-rod, is generally a matched mechanical junction system for substantive force, weight bearing and transmission, such as a set of male ratchet connectors separated by a central rod portion. The male ratchet connectors are inserted into female socket connectors of an appropriate prosthetic using a ratchet retention spring ball system or similar high integrity force and weight bearing mechanical connection.

In an aspect, a system for attachment of a device to a bone is provided. The system includes an internal axial rod with a proximal and distal end that is configured to be inserted and secured into a bone cavity's distal end. The system can also include an internal-external transfer rod with a proximal and distal end mounted into the distal end of the axial rod and a central channel extending through the transfer rod from the proximal end to the distal end and a plurality of attachment rings for attaching at least one tissue or muscle group to the transfer rod. The system also includes a bio-compatible and bio-occlusive artificial membranes (BIOCAMS) lamina, wherein the lamina includes either a polyetheretherketone (PEEK) mesh, a biocompatible polymer, a carbon fiber polymer, an artificial tissue polymer, molded donor tissue, allogenic tissue, a collagen/hyaluronic acid-based tissue, or connective tissue biosynthetic substrate material suitable as webbing.

In another aspect, a system suitable for use as a catheter is provided. The system includes a port head configured for external access to the catheter. The system also includes a top, proximal end of the catheter connected to the port head. The system further includes a bottom, distal end of the catheter extending to a location internal to a body. The system includes internal ports positionable along a length of the catheter configured for passage of fluid through the catheter flow valves arranged within the port head designed to regulate fluid flow through the catheter. The system also includes a bio-compatible and bio-occlusive artificial membranes (BIOCAMS) lamina, wherein the lamina either includes a polyetheretherketone (PEEK) mesh, a biocompatible polymer, a carbon fiber polymer, an artificial tissue polymer, molded donor tissue, allogenic tissue, a collagen/hyaluronic acid-based tissue, and/or equivalent connective tissue biosynthetic substrate material suitable as webbing for surgical implantation into a body.

In yet another aspect, a system suitable for attachment of a device in a transverse direction to a bone is provided. The systems can include a bone implant with a hole extending therethrough and configured to embed into the bone. The system can also include a subcutaneous central mount with a central channel extending therethrough and a plurality of locking channels along its interior perimeter. Further, the system can include a stud connector with a plurality of prongs extending outwardly from exterior surface. Additionally, the system can include a securing mechanism, wherein a central mount extends through the cylindrical hole of the central bone implant and is secured into place, wherein the stud connector locks into the central mount by inserting the prongs into the locking channels and turning clockwise into a locked position. The system can also include a bio-compatible and bio-occlusive artificial membranes (BIOCAMS) lamina, wherein the lamina either includes a polyetheretherketone (PEEK) mesh, a biocompatible polymer, a carbon fiber polymer, an artificial tissue polymer, molded donor tissue, allogenic tissue, a collagen/hyaluronic acid-based tissue, and/or equivalent connective tissue biosynthetic substrate material suitable as webbing for surgical implantation into a body, and wherein the securing mechanism includes a coiled-up spring and/or an elastic material formed into a shape of a helix configured to return to its natural length when unloaded and wherein the central mount is pressure loaded into a locked position.

Additionally, in an embodiment of the present invention, the implant-rods may include infusion and suction ports contiguous with infusion and suction channels internal to the implant-rods. Additionally, an embodiment of the present invention may include a system configured to collect and transmit nerve signaling data to an external processor and further configured to transmit data from the external processor to the nerves. Also, biometric sensors may be included and integrated into the signaling system. The biocompatible signal conduit may include an additional sheathing or sub-conduit which may be fenestrated along portions to allow infusion of fluids such as antibiotics along its length via an external port.

Another embodiment of the present invention may be configured as a single internal to external (SIE) long bone axial implant-rod, which combines the SI axial long bone implant-rod functions and the IE transfer implant-rod functions into a single implant-rod, and may include any selected configuration of BIOCAM and or BIOCAL attachments. The generally central part of this SIE long bone axial implant-rod may include a rectangular or hexagonal region for mechanically screwing the implant-rod into the long bone during implantation. The distal-terminal ends of the SIE long bone axial implant-rod, which lies exterior to the body, are generally a matched mechanical junction system for substantive force, weight bearing, and transmission to an appropriate prosthetic. Additionally, the SIE long bone axial implant-rod may include infusion and suction ports contiguous with channels internal to the implant-rod. Further, the system may include a signal cable/conduit that is configured to collect and transmit nerve signaling data and biometric data to an external processor and may additionally be configured to transmit data information from the external processor to the nerves. The biocompatible signal conduit may include an additional sheathing or sub-conduit which may be fenestrated along portions to allow infusion of fluids such as antibiotics along its length via an external port.

In yet another embodiment of the present invention, a system for attachment of an external object, load, or device in a transverse direction to a bone is provided. It may include a BIOCAM lamina with a usually near-centrally located bone implant stud; which includes an external mechanical junction-connection system for transmission of substantive force and weight bearing capacity to the specific bone, and is concomitantly sized for the host bone size and capacity.

The system can include a subcutaneous central mount with a central channel that can be viewed from at the skin-epidermal surface into which it is inserted and secured with a connector stud which locks into the central mount; There can be an interlocking system, such as a spring coil for pressure loading and locking the connector stud into the implant's central mount. In embodiments, in lieu of a spring coil, the system can include a securing mechanism, the securing mechanism can include a mechanical device, and/or an electro-mechanical device used to store energy and subsequently release it, to absorb shock, and/or to maintain a force between contacting surfaces. In embodiments, the spring coil can include an elastic material formed into the shape of a helix which returns to its natural length when unloaded. The system can include connective tissue, biosynthetic, BIOCAM lamina, or rings for attaching at least one fascia layer and/or one dermal layer to the central bone implant.

The BIOCAM lamina can be constructed from a biocompatible metallic mesh, a biocompatible polymer, a carbon fiber polymer, or an artificial tissue polymer suitable for surgical implantation into the body. The BIOCAM lamina can further include any formation of a transitional webbed area interlaced across a biocompatible scaffolding and may allow for a range of degrees of bio-integration or bio-dissolution. The webbed area can include a generally central area that is more densely woven and has a decreasing density of webbing as it approaches the outer edge of the lamina.

The fascia and dermal layers can be sutured or glued into the webbed area, which may include surface coated molecules of epithelial growth factors or other growth factors. Additionally, the bone implant may include an infusion and suction port contiguous with a channel internal to the implant. The system can further include a rubber or biocompatible plug sized and dimensioned such that the plug secures into the central hole of the bone implant when the connector stud is absent, and would have texture and color similar to the host body.

In an embodiment, the system can provide direct percutaneous mechanical, air, fluid, neural, and biometric interface to a living body. Although embodiments herein are described for human purposes, embodiments of the present invention can apply to an array of vertebrate animals as well. Further, in embodiments, the system can interface with a plurality of materials of a living organism in order to provide extensions of the living organism by enabling an external three-dimensional prosthesis to be connected to the living organism.

Embodiments of the present invention can provide for attachment of an external object or system to a bone, nerve, vascular structure, hollow organ, virtual spaces or soft tissue for functional interface or monitoring. These forms can be aggregated and enhanced for combined and improved functionality. For example, the external object or system can include weapons such as knives and/or firearms, fixed tools and/or rotating tools, remote controlled electro-mechanical devices, and/or robotic devices.

In embodiments, the system can interface with bony interfaces. Further, the system can provide for mechanical integration and be configured for connectivity purposes and for the transfer of weight and forces to and from the body. In embodiments, the system can provide for connection to any bone with a percutaneous bone integrated implant which can have a distal portion that can penetrate through all layers of soft tissue surrounding the bone and can allow for a durable, stable, timely and enduring connection to an exterior object or system.

In embodiments, the system can provide a connection to any bone with a non-percutaneous bone-integrated implant which can be configured to mate to another implant which itself can have a distal portion that can penetrate through all layers of soft tissue surrounding the bone and can allow for a durable, stable, timely and enduring connection to an exterior object or system.

In embodiments, the soft tissues penetrated by the bone percutaneous implants can be either unmodified beyond mere penetration or they can be surgically cinched around the implant for tissue closure, tissue continuity, isolation of the internal bodily environment from the external environment and tissue stability around the percutaneous implant.

In embodiments, the system can provide for a tissue attachment system which can include a central or multifocal transfer-translocation region through which attachment or interface occurs between the internal bodily environment and the exterior of the organism, and may be contiguous with a surrounding surface. In embodiments, the system can include a lamina or mesh, which can allow for single layer or multilayer tissue attachment and integration between the device, system and/or body.

In embodiments, the system can provide for a BIOCAM/BIOCL tissue attachment system which can include a central or multifocal transfer-translocation region through which attachment or interface can occur between the internal bodily environment and the exterior of the organism, and may be contiguous with a surrounding surface. In embodiments, the system can include a lamina or mesh, which can allow for single layer or multilayer tissue attachment and integration between the device, system and/or body.

In embodiments, the system can include central or multifocal transfer-translocation regions which can allow for percutaneous connection to the body via bone attached implants, catheter access to vascular spaces, catheter access to hollow organs such as the bladder, catheter access to a targeted region of an organ such as the renal pelvis, catheter access to virtual spaces such as the pleural space and electronic connectivity to and from chosen points of the nervous system and from biometric sensory elements, and any combination thereof.

In embodiments, the system can provide for an attachment to layers of soft tissue such as epidermis, dermis, fascia, muscle, organs or any bodily tissue and any combination of these layers can be achieved by surgical connection to the BIOCAM/BIOCL tissue attachment device (TAD) and subsequent tissue integration with the tissue attachment device (TAD) by natural tissue healing processes, which may be augmented with growth factors and antimicrobial means and methods.

In embodiments, the system can provide for a mechanism for weight bearing and force translation, simple connectivity or functional connectivity between the musculoskeletal body and an external object(s), air and or fluid transfer ability to and or from the specific locations in the body, targeted and durable neuronal interface and signal transfers to and from the nervous system at those points, and biometric sensory connectivity, and any combination thereof.

BRIEF DESCRIPTION OF THE DRAWINGS

FIG. 6A is an exploded view of the fascia and dermal attachment BIOCAM lamina rings of the present invention;

FIG. 6B is an exploded view of the muscle attachment BIOCL rings of the present invention;

FIG. 6C are alternative lateral views of embodiments of the muscle attachment-BIOCL rings of the present invention;

FIG. 7A is an expanded view of a cross section of the tissue attachment-rings attachment region (TARR) portion to the axial rod-implant portion of the present invention;

FIG. 7B is an expanded view of cross section of the central portion of the BIOCAM/BIOCL attachment-rings of the present invention;

FIG. 7C is an expanded view of the mated cross section portions of the attachment rings to the implant rod tissue attachment-rings attachment region (TARR) portion of the present invention;

FIG. 7D is an expanded view of a cross section portion of the last-on attachment-ring used for securing all the attachment-rings to the axial rod-implant BIOCAM/BIOCL attachment-rings (TARR) portion of the present invention;

FIG. 8A is an expanded top-side view of an embodiment of the present invention;

FIG. 8B is a side view of an embodiment of the present invention showing potential sites of implantation into long bones such as the limb bones;

FIG. 8C is a side view of an embodiment of the present invention showing potential sites of implantation into flat bones such as the pelvic bones;

FIG. 9A is a top view of the retention plug and the rubber or biocompatible plug for the central channel of an embodiment of the present invention;

FIG. 9B is a side view of the retention plug and the rubber or biocompatible plug for the central channel of an embodiment of the present invention;

FIG. 9C is a side view of an embodiment of the present invention showing further detail of the retention spring ball system or similar high integrity force and weight bearing connectivity system as well as the concept of the central plug;

DETAILED DESCRIPTION

Figure 1:
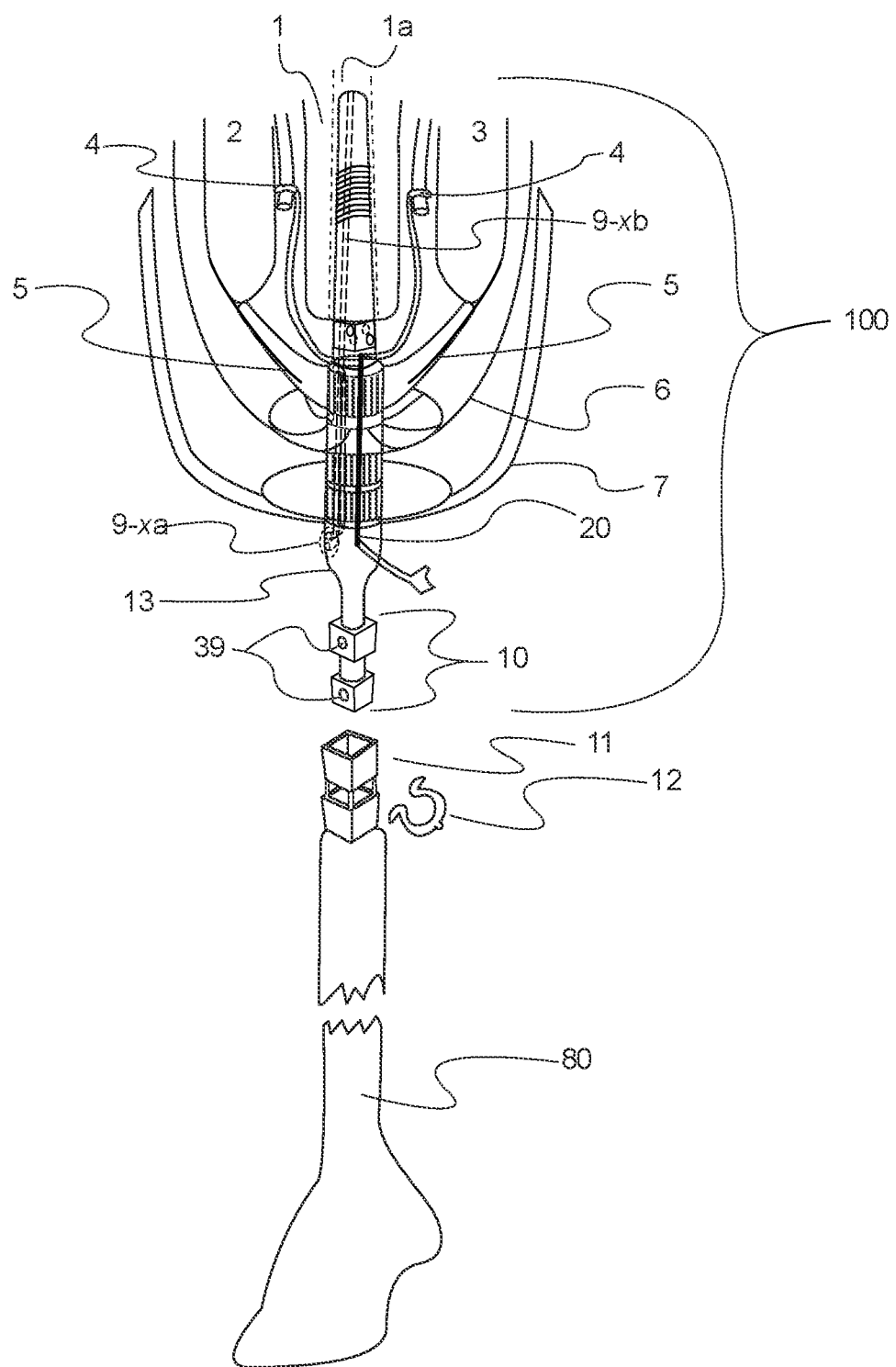
FIG. 1 is front view of an embodiment of the present invention.

Turning to FIG. 1, a view of an embodiment of the present invention is shown with the following general components and interfaces: distal end amputation 1, long-bone prosthetic rod-implant 13 (also shown in FIG. 2) inserted into the long bone medullary cavity 1a, first muscle group 2, second muscle group 3, nerve attachment clips 4, BIOCL muscular attachment-ring 5, BIOCAM fascia attachment-ring 6, BIOCAM dermal/epidermal attachment-ring 7, nerve and biometric signal processor attachment connector 8, infusion-suction port(s) 9-xa, infusion-suction channels 9-xb, prosthetic implant-rod attachment ratchet (male) 10, prosthetic device attachment socket (female) 11, and a prosthetic attachment retention clip 12. Part 80 represents any compatible prosthetic attachment. As shown in FIG. 1, the infusion-suction ports 9-xa can be positioned on a lower portion of the axial implant-rod 13. The infusion-suction ports 9-xa allow both removal of puss and other fluids via the implant from within the contiguous body spaces and allow infusion of saline, antibiotics, and/or other medications via the implant into the contiguous body spaces. Further, the infusion-suction channels 9-xb connect to the infusion-suction ports 9-xa and allow flow into and out of the long bone medullary cavity 1a.

Figure 2:
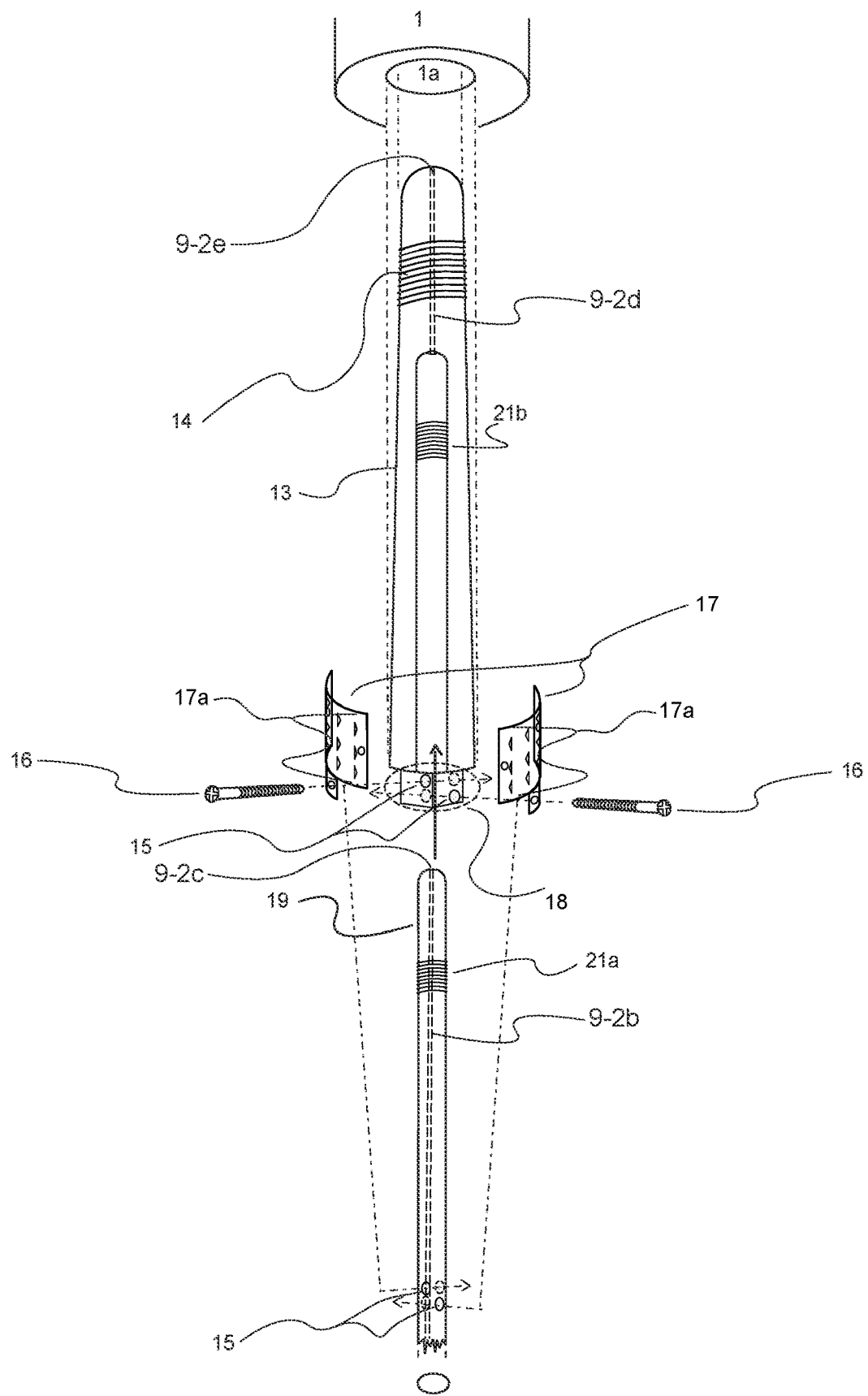
FIG. 2 is an exploded view of an embodiment of the invention of FIG. 1.

Turning to FIG. 2, 4, 5, most of the attachment to the axial skeleton long bone 1, is by the solely-internal (SI) long bone axial implant-rod 13 or the single internal-external (SIE) long bone axial implant-rods 22a, 22b composed of nickel-titanium or equivalent bio-acceptable material. The solely internal (SI) long bone axial implant-rod 13 or the single internal-external (SIE) long bone axial transfer implant-rods 22a, 22b insert into the long bone medullary cavity 1a. Additionally, an optionally included porous nature of the surface of the SI long bone axial implant rod 13 and the SIE long bone axial transfer implant-rods 22a, 22b allows the bone matrix to grow into conformity and mechanically provide for a union with the long bone axial implant-rod.

In an embodiment as shown, the SI long bone axial implant-rod 13 can be hollow for accepting the IE transfer implant-rod 19. The SIE long bone axial implant-rods 22a, 22b provide the combined mechanical interface of the SI long bone axial implant-rod 13 and the IE transfer implant-rod 19 in one element. FIG. 2 illustrates an exploded view of an embodiment of the present invention wherein an internal-external (IE) transfer implant-rod 19 with matching screw interfaces 21a on an upper portion of the exterior of the IE transfer implant-rod 19 mates with matching screw interfaces 21b on an internal portion of the SI long bone axial implant-rod 13. Further, infusion-suction channels 9-2b within the IE transfer implant-rod 19 align with infusion-suction channels 9-2d of the SI long bone axial implant-rod 13. As best seen in FIG. 2, the channels 9-2b have an outlet 9-2c on a tip of the IE transfer implant-rod 19 which aligns with the channels 9-2d on the SI long bone axial implant-rod 13 and allows for fluid to flow into and out of the medullary cavity 1a with an outlet 9-2e on a tip of the SI long bone axial implant-rod 13. Further, infusion-suction channels 9-3a, 9-4a within the SIE long bone axial implant rod 22a, 22b are continuous with the infusion-suction channels 9-3b, 9-4b and have their outlet at the tip of the SIE long bone axial implant rod 22a, 22b at the rod's tip 9-3b, 9-3b.

Embodiments of the SI long bone axial implant-rod 13 and the SIE long bone axial transfer implant-rods 22a, 22b may have screw-like proximal segments 14. The screw-like section transfers weight bearing forces from the long bone axial implant to the long bone 1, or from the long bone 1 to the either the SI long bone axial transfer implant-rod 13 or the SIE long bone axial implant-rods 22a, 22b and thereby to the entire implanted transcutaneous system 100. The entire implanted transcutaneous system 100, can have clamps 17, which clamp to the external surface-periosteum-cortical surface of the long bone by appropriately shaped clamps 17 with pointed/ridge-like peaks 17a that grasp the long bone mechanically.

These clamps can mount to the long bone axial implant-rod by fixation screw 16 through the clamps and through the distal end of the long bone axial implant-rod 13, 22a, 22b via screw bores 15. This arrangement transfers external rotational forces from the prosthetic 80 to the entire implanted system 100 and subsequently to the long bone. Possible extrinsic forces that could pull at the implant would include turning a knob or a screwdriver or the kickback torsion from a power drill. Additionally, this segment of the long bone axial implant-rods 13, 22a, 22b with the bore holes 15 may have a square, or hexagonal segment 18 which allows for mechanically turning the long bone axial implant-rods during implantation.

Additionally, the long-bone axial implant-rod fixation screws 16 extend through the long bone bores holes 15 and into the medullary shaft of the long bone providing additional mounting stability against forces transmitting from the external environment to long bone of the body. The hexagonal segment 18 can include multiple bore holes 15 and fixation screws 16, and in embodiments not shown may include one and/or a plurality of bore holes 15 and fixation screws 16.

Figure 3:
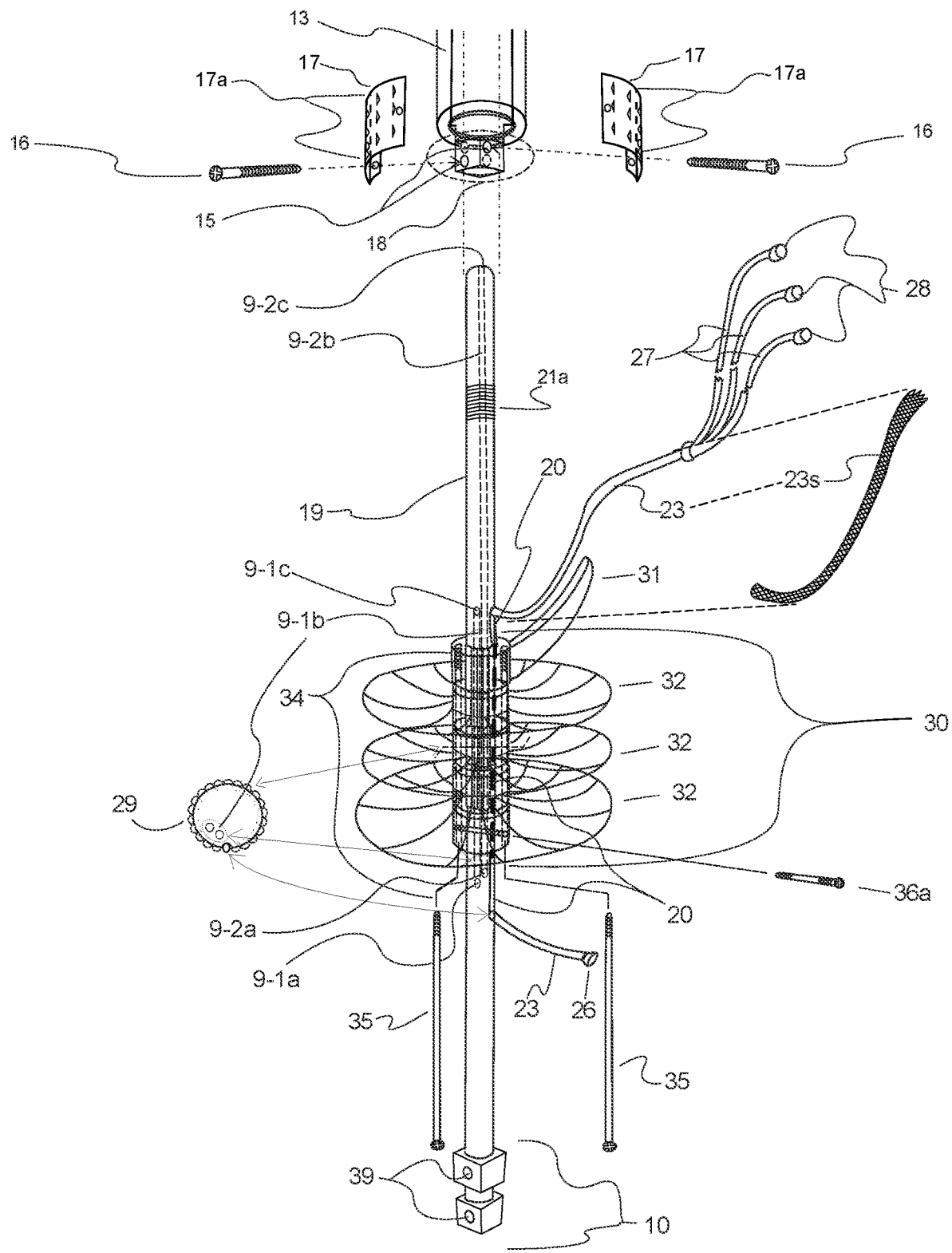
FIG. 3 is an exploded view of an embodiment of the invention of FIG. 1.

The fixation clamps 17 can have several rows of ridged peak mounting teeth 17a that grip into the external cortical bone—periosteum as a mechanical-structural-force interface. The fixation screws 16 can also penetrate through the periosteum and into the endosteum for additional mechanical fixation. The solely internal (SI) long bone axial implant-rod 13 may be hollow and can accept an inserted internal-to-external (IE) transfer implant-rod 19. The IE transfer implant-rod 19 (as shown in FIGS. 2 and 3) can provide for the physical connection between the entire implanted system 100 and the soft tissues of the limb and the external environment.

Figure 4:
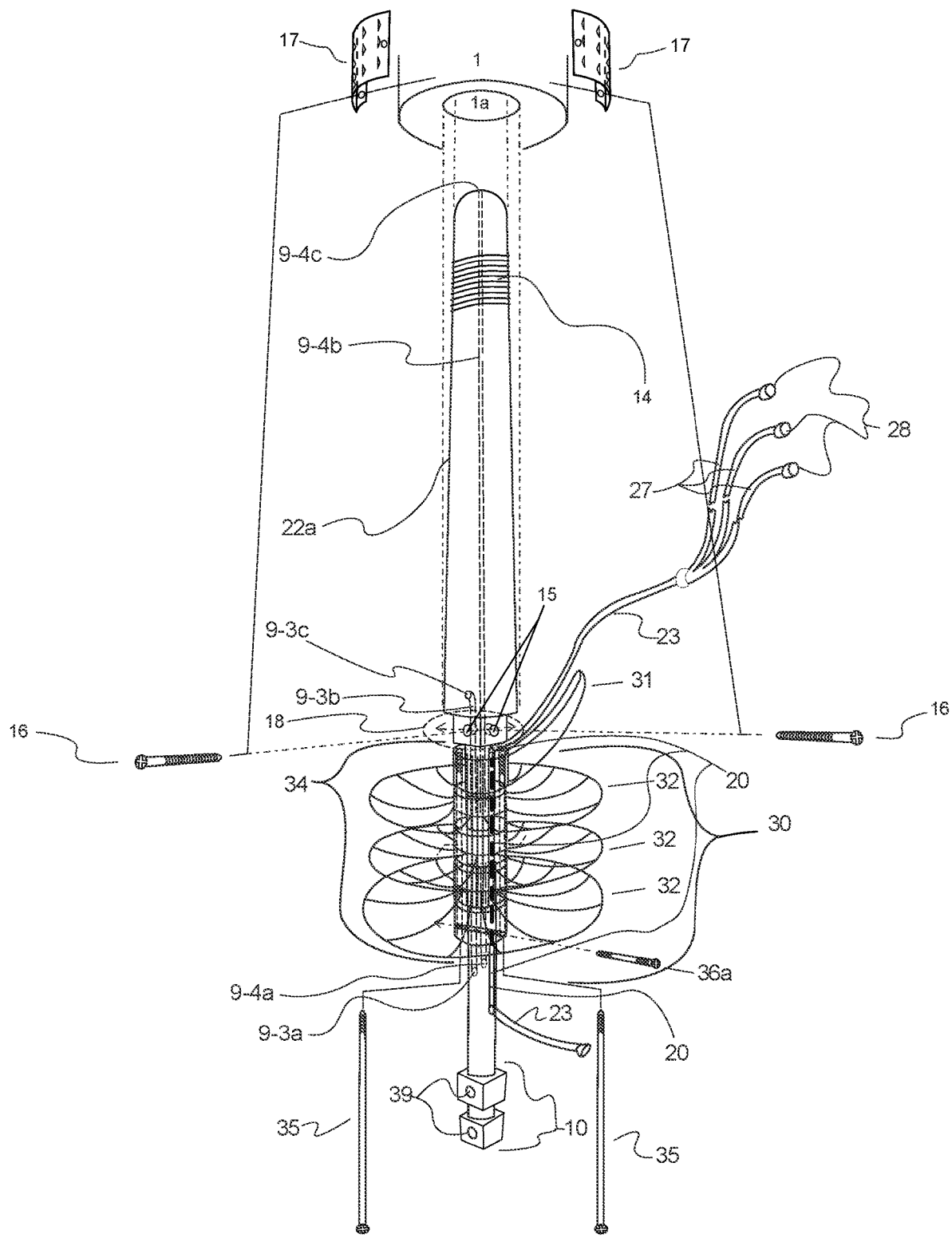
FIG. 4 is an exploded view of an embodiment of the invention of FIG. 1.
Figure 5:
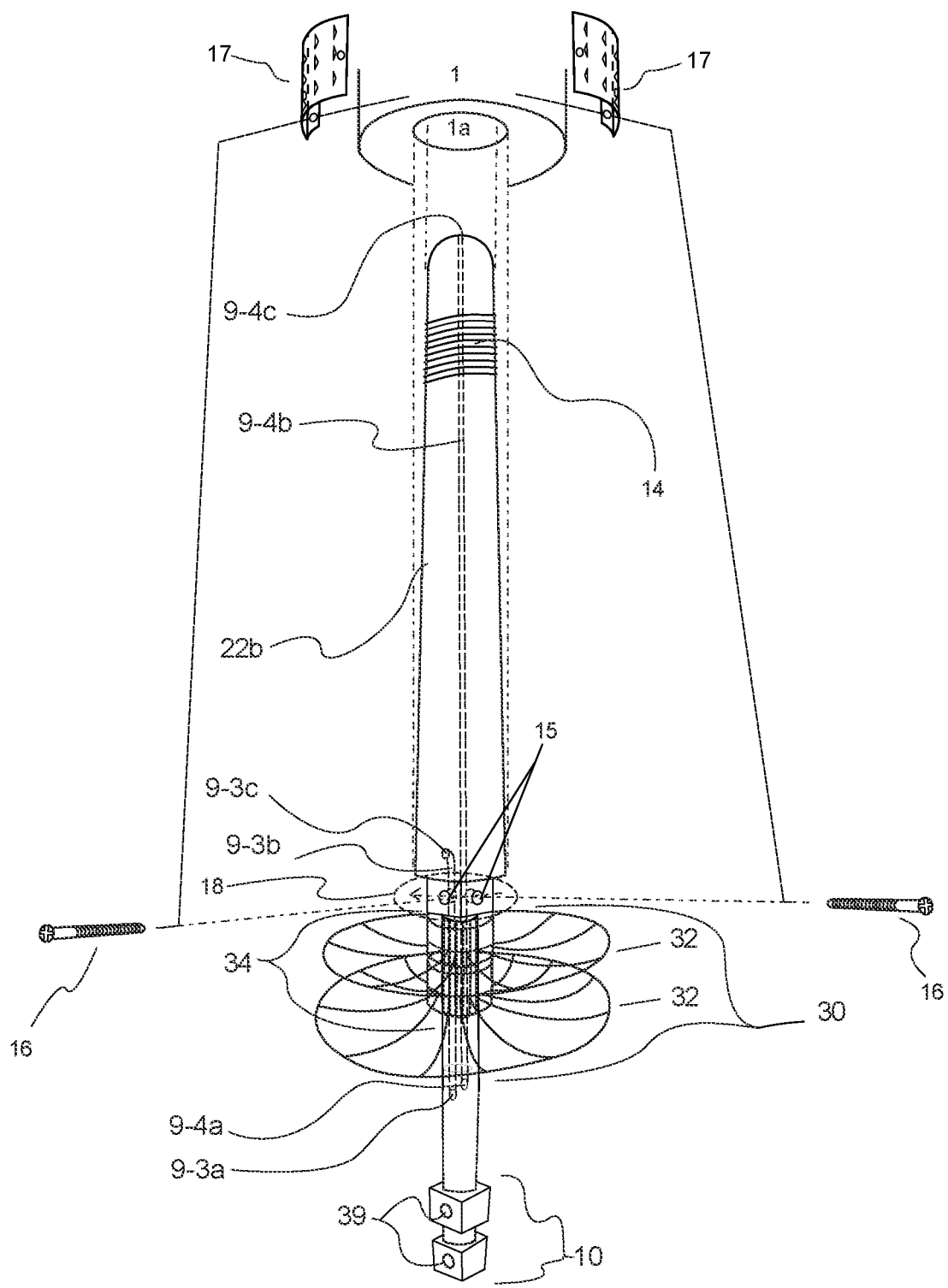
FIG. 5 is an exploded view of an embodiment of the invention of FIG. 1.
Figure 7E:
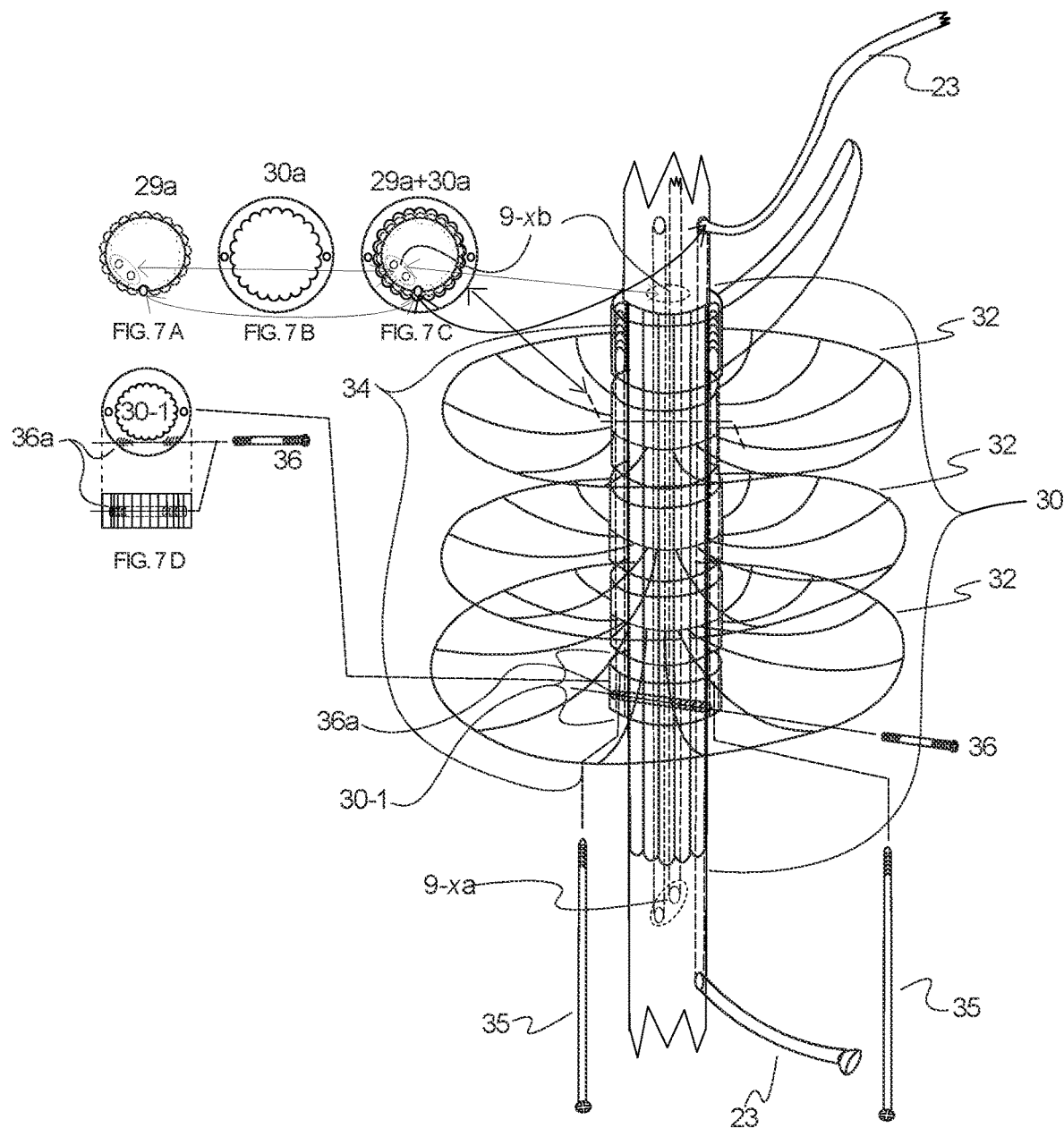
FIG. 7E is an expanded view of the BIOCAM/BIOCL tissue attachment-ring attachment region (TARR) of the implant-rod with characteristic attachment-rings, the various bore holes and screws which secure the attachment-rings in place and additionally demonstrate the infusion/suction ports and the signaling cables integrated into this portion of the implant-rod.

For the SIE long bone axial transfer implant-rods 22a, 22b, (as shown in FIGS. 4 and 5) the proximal end provides the physical connection between the long bone 1 and the distal end and connects to the external environment. The IE transfer implant-rod 19 inserts into the long bone axial implant-rod 13 and screws into place with matching screw interfaces 21a, 21b, to mount it within the long bone axial implant-rod 13 and provide for substantive force and weight bearing transmission from the long bone 1 to the long bone axial implant-rod 13 and to the IE transfer implant-rod 19. The IE transfer implant-rod 19 and the SIE long bone axial implant rod 22a, 22b interface to the soft tissues of the limb by various BIOCAM lamina-rings 31 and BIOCL 32. It connects to external prosthetics via a matched mechanical junction system for substantive force and weight bearing and transmission to a male/female dual ratchet-socket mechanism, 10 and 11 respectively.

The SI long bone axial implant-rod 13 and the SIE long bone axial implant rod 22a, 22b have bore holes 15 through which fixation screws 16 attach fixation clamps 17 and into the long bone itself. Additionally, the segment of the SI long bone axial implant-rod 13 and the SIE long bone axial implant-rod 22a, 22b with the bore holes 15 may have a square, or hexagonal segment 18 which allows for mechanically turning the long bone axial implant-rod 13, 22a, 22b into the long bone 1 during implantation. The IE transfer implant-rod 19 is inserted and screwed into the SI long bone axial implant-rod 13 by matching screw interfaces 21a and 21b. The IE transfer implant-rod 19 has an exterior screw segment 21a which mates with the SI long bone axial implant-rod's 13 interface interior bore screw segment 21b.

The IE transfer implant-rod 19 is affixed to the distal end of the long-bone axial implant-rod 13 by screw bores 15 and fixation screws 16.

Additionally, the IE transfer implant-rod 19 fixation screws 16 and SIE long bone axial implant-rod 22a, 22b fixation screws 16 extend through the long bone bores holes 15 and into the medullary cavity 1a of the long bone 1 providing additional mounting stability against forces transmitting from the external environment to long bone 1 of the body. The diagram shows multiple bore holes 15 and screws 16, but not all may be necessary to be utilized at the time of implantation.

The fixation screws 16 also mechanically attach the axial implant-rod to the long bone by clamps 17 with pointed-ridged peaks 17a gripping the external surface-periosteum-cortical surface of the long bone 1. The fixation screws 16 also penetrate through the periosteum and into the endosteum for additional mechanical fixation.

Turning to FIGS. 3-9, "PEEK" stands for polyetheretherketone, which is a semi-crystalline, high temperature plastic. It is chosen to represent any selection of a large family of bio-neutral polymers available for surgical implantation purposes. The BIOCAM lamina can be constructed either from a PEEK mesh, a biocompatible metallic mesh, a biocompatible polymer, a carbon fiber polymer, an artificial tissue polymer, molded donor tissues, allogeneic tissue, collagen/hyaluronic acid based tissue, and/or any other equivalent connective tissue biosynthetic substrate material suitable as webbing for surgical implantation into the body.

The BIOCAM lamina can further include any formation of transitional webbed areas interlaced across a biocompatible material scaffolding and may allow for a range of degrees of bio-integration or bio-dissolution. The webbed area can include a generally central area that is more densely woven and has a decreasing density of webbing as it approaches the outer edge of the lamina. The host body's tissue layers can be sutured or glued onto and into the webbed areas of the lamina. The lamina materials may further include surface coated molecules of epithelial growth factors or other growth factors. Biocompatible linkages (BIOCLs) for attachment to tendon & muscle groups are generally made of similar materials as BIOCAMs. BIOCAMs and BIOCLs allow for "cytointegration" and "organointegration" of the BIOCAMs and BIOCLs with bodily tissues.

Figure 10:
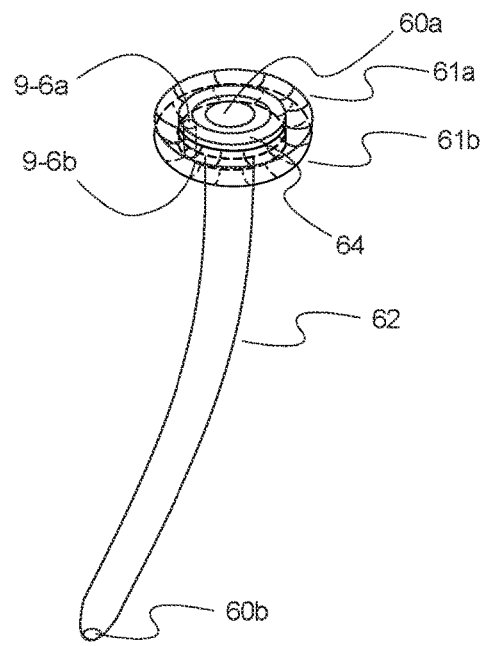
FIG. 10A is a top-side view of an embodiment of the present invention showing an infusion-suction ported, dual BIOCAM lamina based catheter for hollow organs, such as a suprapubic catheter.
FIG. 10B is a top-side view of an embodiment of the present invention showing a triple infusion-suction ported, single BIOCAM lamina based catheter for 'potential-space' or intra-organ space, such as for a pleural space catheter or a renal pelvis catheter, and includes a proximal tissue flushing port.
FIG. 10C a top-side view of an embodiment of the present invention showing a quad ported, single BIOCAM lamina-based catheter for direct or tunneled intravenous access and includes a port for subcutaneous tissue flushing along the through-tissue transit-region.
Figure 10:
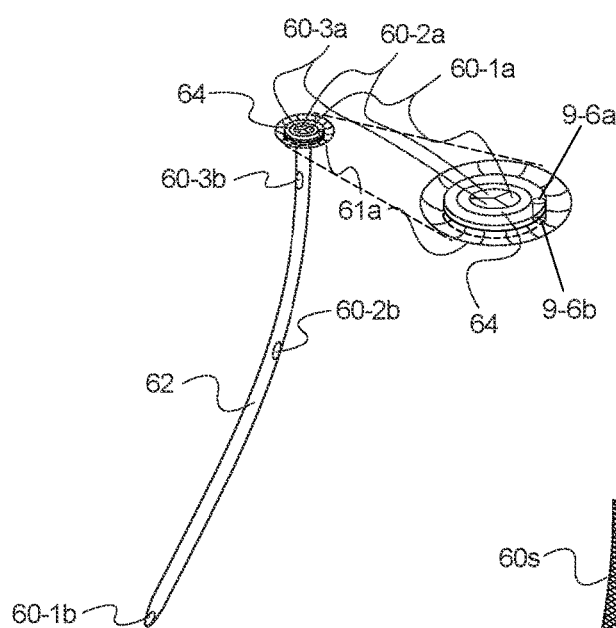
Figure 10:
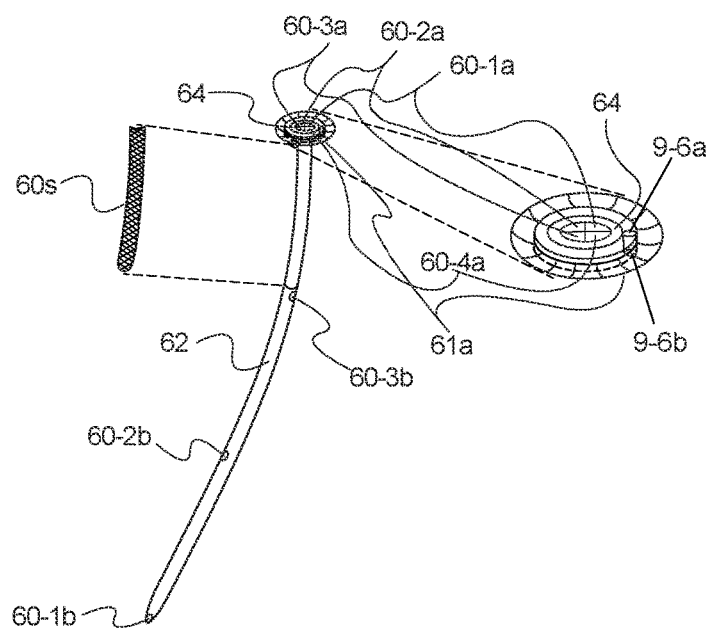

In FIGS. 1, 3, 4 the IE transfer implant rod 19 and the SIE long bone axial implant-rod 22a may have an included channel 20 which may be a groove along the rod's edge, or a channel within the IE transfer implant-rod 19 or the SIE long bone axial implant rod 22a through which a sealed micro-wire cable 23 which is insulated with PEEK, a carbon fiber or other bio-acceptable dielectric material, attaches to a modified Utah Array 46, in FIG. 10, which itself interfaces to a nerve/nerve bundle 46, 47. Additionally, optionally included biometric sensors can attach to the same transmission bundle.

The micro wire 23 runs from inside the limb or body region from the nerve attachment sites and biometric sensor sites, then passes down the IE transfer implant-rod 19 or the SIE long bone axial transfer implant-rod 22a at the channel 20 and exits those implant-rod channels to the exterior of the body, where it can attach by an appropriate connector to an external processor connection 26. The biocompatible signal conduit may have an optionally included additional sheathing or sub-conduit which may be fenestrated 23s along portions to allow infusion of fluids such as antibiotics along its length via an external port.

The micro-wire cables 24 can come in bundles 27, and attach to micro connectors 28 that clamp directly onto an associated nerve or nerve bundle (see FIG. 10). The IE transfer implant-rod 19 and SIE long bone axial transfer implant-rods 22a, 22b have a Tissue Attachment BIOCAM lamina-Ring and BIOCL Region (TARR) 30 comprised of gear-like pitches-teeth-ridges shown in cross-section 29a to which mating slotted ring hubs 30a of the BIOCAM/BIOCL tissue rings shown in cross section 30a allow mechanical attachment, force translation, environmental barriers and various connective purposes at various tissue layers.

Referring to FIGS. 3, 4, 5, 6A-6C, and 7A-7E, in general, there is an attachment-ring for any BIOCAM lamina-ring 31 and BIOCL 32 for limb tissue attachments. BIOCL-muscle attachment-rings may be for one, two, three, four or more associated muscle groups 31. There are BIOCAM lamina-rings 31 attachments for tissue closure at the fascia and dermal layers.

Each BIOCAM lamina-ring will attach by sliding its hub 30a into position along the TARR 30 (tissue attachment-ring region). BIOCAM lamina-rings 31 and BIOCL rings 32 are fastened together by longitudinal bore holes 34 and screws 35 mounted. The most distal ring 30-1, which may be a mounting ring not otherwise used for tissue connection, is mounted via a transverse bore hole 36a mounted screw 36. Optionally, each attachment-ring may be each mounted via a similar bore and screw method.

At the end of the IE transfer implant-rod 19, or SIE long bone axial transfer implant-rods 22a, 22b and external to the limb or other bodily attachment point, is a dual ratchet type connector 10 sized for appropriate load bearing.

There is a simple ratchet retention spring-ball system 39 for initial connection. Between the two ratchet areas is a central rod area for a retention clip 12 to maintain definitive attachment of external prosthetic devices. Optionally included is any form of appropriate attachment hardware design configuration. In embodiments not shown, the system can include attachment devices between the implant 100 and the prosthetic 80 such as, but not limited to, magnetic coupling devices, electro-mechanical locking devices, rigidly fixed connectors, quick connect and disconnect connectors, snap-on/snap-off devices, and twist and click attachment connectors.

The BIOCAM lamina-rings 31 and BIOCLs 32 attach to the IE transfer implant-rod 19 or the SIE long bone axial transfer implant-rod 22a, 22b at the TARR-tissue attachment-ring region 29 of the implant-rods at the tissue ring central hubs 30a via matting gear-like pitches-teeth-ridges shown in FIGS. 3-7. The BIOCL rings that attach to muscle groups include from one to four or more attachment flanges 37 in FIGS. 6B, 6C, designed as levers connecting between muscle/tendons and the IE transfer implant rod 19 or the SIE long bone axial transfer implant-rods 22a, 22b.

Additionally, the adjacent, minimally weight bearing long bone, such as the radius-ulna or tibula-fibula which is not joined to the IE transfer implant-rod or the SIE long bone axial transfer implant-rod TARR, can be attached to a muscle flange via screw bore holes 38 and screws 38a for concurrent fixation. Muscle fibers 5 or tendons are surgically attached to the flanges 37 via suturing, stapling, gluing or similar means to a mesh network 40, 41 to provide intralimb force transfer from the host body to the rod assemblies.

The BIOCAM lamina-rings 31, and BIOCLs 32 may have a metal, including nickel-titanium, mounting scaffold 40 as a skeletal framework, with a biocompatible webbing-mesh 41—described in section 0045—for sutures, staples, glue, or similar means for cyto-cellular attachment. The BIOCAM lamina-rings for fascia and dermal attachment may have a transitionalweb/mesh 42 with the central area being a solid biocompatible material attached and may be based upon a nickel-titaniumscaffold.

This transitions to a progressively "looser" web zone of the specific biocompatible material-lamina and ends at the outer ring of metal scaffold. The mesh and sub-mesh may be composed of a PEEK mesh, a biocompatible metallic mesh, a biocompatible polymer, a carbon fiber polymer, an artificial tissue polymer, molded donor tissues, allogeneic tissue, collagen/hyaluronic acid based tissue, any other equivalent connective tissue biosynthetic substrate material suitable as webbing for surgical implantation into the body.

It is into this biocompatible webbing 41 which the fascia 6 or dermal 7 layers are sutured, stapled, glued or similarly joined, and into which the fascia and dermal will grow and interweave with for exclusion of any external environment when fully healed. Such interfaced healing may be augmented by the use of epidermal growth factors or vascular endothelial growth factors, or similar endovascular growth promoting molecules.

Referring to FIGS. 1, 3, 4 and 11A-11B, the micro-wire cables 23 attached to typically to appropriately sized sensor/stimulator Utah Array matrix 44 arising from a semiconductor substrate 45 and mounted within nerve/bundle clips 43. The Utah Array penetrate through each associated nerve sphingomyelin nerve sheath 46a into the nerve cytoplasm 46b itself and clamps 43 onto the nerve(s) 46. The nerve(s) 46 are penetrated by appropriately sized modified Utah Array, potentially of carbon fiber spindles or similar bio-neutral conductor, which are integrated onto silicon on insulator (SOI) or similar semiconductor substrate, typically with an integrated digital signal processor (DSP) which uses analog to digital conversion, signal compression, time division multiplexing or similar asynchronous to synchronous multiplexing of data into a single or few digital streams for transmission through the micro-wire cable to external processing.

Figure 11A:
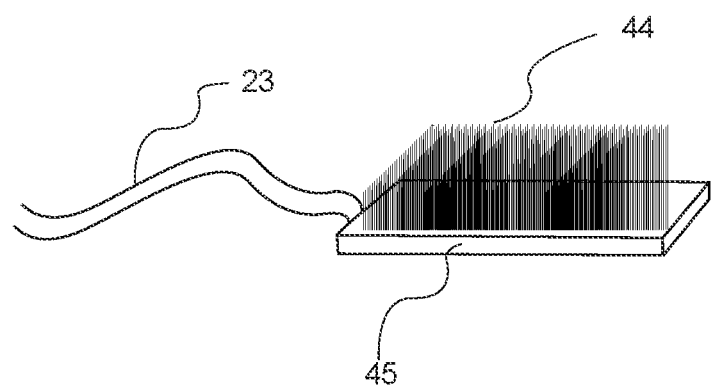
FIG. 11A is a side view of the Utah Array portion of the nerve interface and signaling cable portion of the present invention.
Figure 11B:
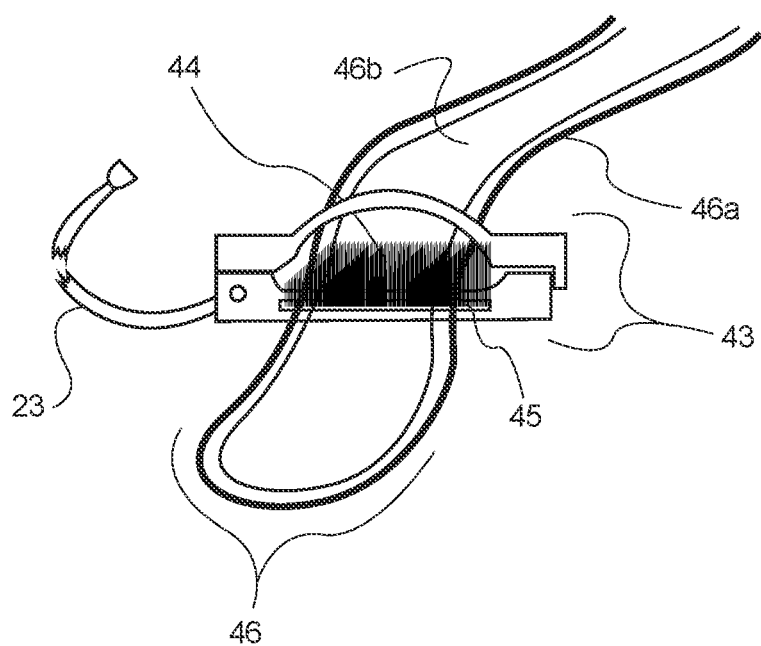
FIG. 11B is a side perspective view of the nerve clip of the present invention.

External feedback to the nervous system is via the essentially reverse process. Other biometric data can also be integrated into the same data flow. FIGS. 11A and 11B show the orientation of the Utah array 44 longitudinally so spindles either increase or decrease in height and depth of nerve penetration along the length of the nerve, while other optional orientations can also occur.

The SOI-semiconductor substrate long dimension potentially ranges from about 0.5 mm to about 5 mm, according to the size of the target nerve/bundle. The Utah Array 44 is potentially composed of carbon fibers or other semiconductor spindles measuring about 1-100 um diameter spaced about 1 um-1 mm apart, and are about 0.5 mm to about 5 mm high, and are optionally partially coated with sphingosine, or another nerve sheath cell related molecule. The spindle coating allows for a more integrated transmembrane entry through the nerve sheath cell membrane and into the cellular cytoplasm.

Human nerves typically are 0.1-5 micrometers in diameter. Current generation integrated circuit transistor gate size is about 3-5 nm. The DSP is configurable after implantation to group sets of the UA spindles into functional groups and sensory or excitatory pathways.

The DSP detects the changes in the nerve cells' ion fluxes, surface potentials and internal voltages. It digitizes that information (at potentially 8-24 bit resolution) and serializes the information to allow connection 8 to exterior processing elements for transmission of the nerve signal data to the external environment. The nervous system connection and processing system also allows feedback signals to be returned to the nerve bundle by digital to analog processing via the same UA/DSP and potentials gated out to the UA array/nerve interface. Biometric sensors can transmit data along the same digital path.

Referring to FIGS. 8A, 8B, 8C, 9A, and 9B, an additional type of transverse prosthetic attachment 48 is shown mounted in transverse-perpendicular direction to a particular bone, such as the radius-ulna (forearm) 49a or ileum (lateral pelvis) 49b. These implants are meant for load bearing, load stabilization and external accessory attachment but not for high impact or high torsion connections.

The transverse bone implant 48 has a central-anchor 52 which is a metal, such as nickel-titanium, or carbon fiber or other appropriate highly tensile bio-neutral material. The implant 48 has BIOCAM lamina-ring zones 50 for attachment to fascia and dermis, similar to areas 32, 40, 41 and 42 in FIGS. 6A and 6B. The central-anchor has a screw-like region 52a which provides durable mechanical interface to cortical and/or medullary bone. Additionally, there is an engagement-region 53 comprised of gear-like pitches-teeth-ridges, which provides rotational stability to the implant. Additionally, an optionally included porous nature of the engagement-region 53 and the central-anchor screw-like region 52a allows the bone matrix to grow into conformity and mechanical union with the central-anchor.

Additionally, an optionally included long mounting screw 55 transverses through the bore 55a in the anchor's rim 51 and anchors through the periosteum into the endosteum to provide supplemental resistance to torsion and longitudinal forces that could dislodge the anchor. The central-anchor itself has a central channel 56 that is visible at the skin surface. A pronged-stud connector 57 fits into the central channel 56 and provides mechanical connection to any appropriate mount via at least one pronged-studs 57a that inserts into locking channels 58 and the pronged-stud 57a turns into a locked position and is spring 59 pressure loaded into a held-retained position. Other mechanical junction methods are optional between the central-anchor and an exterior attachment.

Any attachment of appropriate size and purpose could mount to the accessory pronged-studs, such as a load bearing backpack, additional attachments to a large manually operated tool, and so on.

A rubber or biocompatible plug 57-2 inserts into the empty stud's central channel to keep the connector clean between uses and would have texture and color similar to the host body.

It is an embodiment of the present invention to provide a new system and method for improving percutaneous, biocompatible and bio-occlusive attachment of medical devices including a wide array of tubes and catheters. These percutaneous interfaces potentially include mechanical interface—including air and fluid interface, neuronal interface, and sensory/biometric interface. In an embodiment of the present invention is a system to provide placement of a percutaneous catheters or tubes which have (a) bio-compatible and bio-occlusive artificial membranes (BIOCAMs) tissue attachment lamina to allow for attachment to any epithelial, mesothelial or endothelial derived tissue layer such as dermal, fascial, endothelial, mucosal, and pleural tissue layers and/or potentially multi-flanged biocompatible linkages (BIOCLs) for attachment to tendon & muscle groups for prolonged or semi-permanent periods of placement, which we call cytointegration and organointegration.

The BIOCAM lamina may have portal head through the lamina itself, typically within the central region, for external connection to the internally based catheters or tubes. The portal head contains all the ports for that particular catheter or tube. FIGS. 10a, 10b, and 10C, show three types of BIOCAM based catheters. In FIGS. 10a, 10b, and 10c, 60a, 60-1a, 60-2a, 60-3a, 60-4a are the external access ports to the catheter. The catheters themselves 62 may have as many sub-ports and channels as is deemed needed and reasonable for manufacture and use. The BIOCAM catheter may have an optionally included additional sheathing or sub-conduit which may be fenestrated 60s along portions to allow infusion of fluids such as antibiotics along a portion of its length via an external port 9-6a. This catheter sheathing would typically sheath the portion of the catheter that transitions through other tissues as it extends towards its intended distal position, for example the subcutaneous tissue of the back and retroperiteum for a percutaneous nephrostomy tube. The external access ports will likely have multi-layer connection port head 64. The portal head contains all the device's ports, negates leakage and allows controlled drainage, suction or infusion of fluids or air. The portal head likely has several mechanically joined layers that may include a lamina-integrated base layer with bidirectional valves, an 'inner' adaptor that screws or snaps into and rests upon the base layer and provides high pressure sealant connectivity and secondary flow valves and is a replaceable long-term device. A secondary adaptor screws or snaps into the 'inner adaptor and rests upon the inner adaptor and further provides a secondary high pressure sealant layer and allows for selectable connectivity.

Finally, a cap optionally sits upon the secondary adaptor, and provides occlusive seal and skin tone and texture blending. The inner, secondary, and cap portal head adaptors are removable and allow replacement all but the base layer of the portal connection head for general replacement reasons, non-sterile cleaning, sterile cleaning, and updated connectivity. The internal ports themselves 60b, 60-1b, 60-2b, 60-3b are internal to the organ or bodily region and are continuous, for fluid and air flows, with the catheters' external ports of the same base number and letter pair (each 60a is continuous with 60b). The flows are regulated external the portal head by external devices, except for the flow valves within the portal head itself, which keeps any flow from occurring unless a port control cap is placed. The BIOCAM lamina 61a, 61b attach to appropriate tissue layers such as dermal and mucosal layers (i.e. bladder wall) to provide isolation of the exterior environment 61a and from leakage from the internal organ environment 61b into adjacent soft tissues.

The non-catheter-based catheter portal head infusion port 9-6a, 9-6b allows for infusion-suction of any antiseptic-antimicrobial fluids that are necessary to episodically and/or repeatedly, sterilize the local soft tissue environment of the catheter itself either directly at the internal portion of the portal head or into transitional tissues via a catheter sheath 60s. For these catheters, the BIOCAM lamina may be biocompatible and bioabsorbable, perhaps upon a carbon fiber or manufactured biologic tissue mesh, to allow integration of the catheter lamina into the surrounding tissue except for the portal head device itself. If extraction is necessary, the portal head device and catheter would be removed but the bodily integrated lamina would likely remain in-situ/in-place.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail.

Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

The present invention has been described with reference to the preferred embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

What is claimed is:

1. A system suitable for use as a semi-permanent percutaneous interface configurable as a catheter comprising:
   a distal, partially external port head configured for external access to the catheter;
   a distal, top end of the catheter connected to the port head;
   wherein the port head is semi-permanently attached to adjacent tissue layers;
   a proximal, internal, bottom of the catheter extending to an internal location internal to a body;
   internal ports positionable along a length of the catheter configured for passage of fluid through the catheter;
   flow valves arranged within the port head designed to regulate fluid flow through the catheter; and
   bio-compatible and bio-occlusive artificial membranes (BIOCAMS) lamina providing attachment of a port head lamina and/or other concomitant BIOCAM lamina to adjacent tissue layers, including any epithelial, mesothelial or endothelial derived tissue layer such as epidermal, dermal, fascial, endothelial, endovascular, mucosal, bone, pleural, peritoneal, muscular, organ, organ region, organ layer, organ component or organ compartment or any other bodily tissue and/or any combination of these tissues and layers, wherein the lamina is configured to provide isolation of the exterior environment or any adjacent tissue, layer, component, compartment, region, or environment, and to minimize leakage from a specific internal bodily or organ environment into adjacent soft tissue or bone.

2. The system of claim 1 wherein the catheter includes infusion and suction ports contiguous with infusion and suction channels of the port head configured to allow infusion of fluids along its length via its external ports at the port head.

3. The system of claim 1 wherein the BIOCAMS lamina is configured to be biocompatible and bioabsorbable, including a carbon fiber or manufactured biologic tissue mesh, to allow integration of the catheter lamina into the surrounding tissue except for the portal head device itself, the portal head device and catheter is removable and the integrated lamina remains in place.

4. The system of claim 1 wherein the BIOCAMS lamina further includes formation of transitional webbed areas interlaced across a biocompatible material scaffolding designed to allow for a range of degrees of bio integration or bio-dissolution, the webbed area also includes a generally central area that is more densely woven and has a decreasing density of webbing as it approaches the outer edge of the lamina.

5. The system of claim 1 further including additional sheathing or sub-conduit configured to be fenestrated along portions to allow infusion of fluids along a portion of its length via an external port.

6. The system of claim 1 wherein the BIOCAMS lamina includes another port head through the lamina positionable on about a central region configured for external connection to internally based catheters.

7. The system of claim 1 further comprising a non-catheter portal head infusion port structured to allow for infusion and/or suction of antiseptic-antimicrobial fluids utilized to clean and/or sterilize a local soft tissue environment of the catheter.

8. The system of claim 1 further comprising an inner adaptor configured to securely fit and rest upon a base layer designed to provide high pressure sealant connectivity and wherein the inner adaptor includes replaceable secondary flow valves.

9. The system of claim 1 further comprising multi-flanged biocompatible linkages (BIOCLS) configured for attachment to tendon and muscle groups.

10. The system of claim 1 further comprising tissue attachment devices (TAD) designed for attachment to layers of soft tissue such as epidermis, dermis, fascia, muscle, organs or any bodily tissue and/or any combination of these layers.

11. The system of claim 1 further comprising biometric sensors integrated into the system.

* * * * *